(12) United States Patent
Griffin (10) Patent No.: US 9,323,005 B1
(45) Date of Patent: Apr. 26, 2016

(54) REDIRECTING ELECTROMAGNETIC RADIATION

(71) Applicant: InnovaQuartz LLC, Pheonix, AZ (US)

(72) Inventor: Stephen E. Griffin, Peoria, AZ (US)

(73) Assignee: InnovaQuartz LLC, Pheonix, AZ (US)

( * ) Notice: Subject to any disclaimer, the term of this patent is extended or adjusted under 35 U.S.C. 154(b) by 0 days.

(21) Appl. No.: 14/578,739

(22) Filed: Dec. 22, 2014

(51) Int. Cl.
G02B 6/26 (2006.01)
G02B 6/32 (2006.01)
G02B 6/42 (2006.01)
C03B 37/00 (2006.01)
A61B 18/22 (2006.01)
C03B 37/012 (2006.01)

(52) U.S. Cl.
CPC . *G02B 6/32* (2013.01); *A61B 18/22* (2013.01); *C03B 37/01211* (2013.01); *A61B 2018/2266* (2013.01)

(58) Field of Classification Search
CPC ....... G02B 6/32; A61B 18/22; C03B 7/01211
USPC ...................................... 385/33, 32
See application file for complete search history.

(56) References Cited

U.S. PATENT DOCUMENTS

| | | | |
|---|---|---|---|
| 4,669,467 A | 6/1987 | Willett et al. |
| 4,672,961 A | 6/1987 | Davies |
| 4,732,448 A | 3/1988 | Goldenberg |
| 4,740,047 A | 4/1988 | Abe et al. |
| 5,061,265 A | 10/1991 | Abela et al. |
| 5,074,632 A | 12/1991 | Potter |
| 5,269,777 A | 12/1993 | Doiron et al. |
| 5,292,320 A | 3/1994 | Brown et al. |
| 5,343,543 A | 8/1994 | Novak et al. |
| 5,354,294 A | 10/1994 | Chou |
| 5,428,699 A | 6/1995 | Pon |
| 5,486,171 A | 1/1996 | Chou |
| 5,495,541 A | 2/1996 | Murray et al. |
| 5,496,307 A | 3/1996 | Daikuzono |
| 5,496,308 A | 3/1996 | Brown et al. |
| 5,498,260 A | 3/1996 | Rink et al. |
| 5,509,917 A | 4/1996 | Cecchetti et al. |
| 5,512,078 A | 4/1996 | Griffin |
| 5,530,780 A | 6/1996 | Ohsawa |
| 5,537,499 A | 7/1996 | Brekke |
| 5,562,657 A | 10/1996 | Griffin |
| 5,571,099 A | 11/1996 | Purcell et al. |
| 5,695,583 A | 12/1997 | Bergh et al. |
| 5,807,390 A | 9/1998 | Fuller et al. |
| 5,824,005 A | 10/1998 | Motamedi et al. |
| 6,246,817 B1 | 6/2001 | Griffin |
| 6,270,492 B1 | 8/2001 | Sinofsky |
| 6,284,085 B1 | 9/2001 | Gwo |
| 6,398,778 B1 | 6/2002 | Gu et al. |

(Continued)

*Primary Examiner* — Jerry Blevins
(74) *Attorney, Agent, or Firm* — Synthesis Intellectual Property, LLC (57) ABSTRACT

Herein is provided a side fire optical device for redirecting electromagnetic radiation, methods of its manufacture, and methods of its use. The herein described side fire optical device minimizes potential Fresnel reflections at fused surfaces and eliminates Snell and Fresnel reflections in a self-contained lateral output assembly (within which a transmitting optical fiber conduit may be subsequently attached). The construction of which involved lower cost raw materials and fewer manufacturing steps; provide a side fire fiber where the protective cap can be replaced interoperatively and even intraoperatively; and provide mechanisms and processes for altering the size or shape of the output spot without altering the lateral fiber design.

18 Claims, 10 Drawing Sheets

(56) References Cited

U.S. PATENT DOCUMENTS

| | | | |
|---|---|---|---|
| 6,474,108 B2 * | 11/2002 | Onishi et al. | 65/397 |
| 6,522,806 B1 | 2/2003 | James et al. | |
| 6,687,436 B2 | 2/2004 | Griffin | |
| 6,712,526 B1 | 3/2004 | Fleenor | |
| 6,829,411 B2 | 12/2004 | Easley | |
| 6,986,764 B2 | 1/2006 | Davenport et al. | |
| 7,463,801 B2 | 12/2008 | Brekke et al. | |
| 7,909,817 B2 | 3/2011 | Griffin et al. | |
| 8,073,297 B2 | 12/2011 | Griffin | |
| 2005/0165279 A1 | 7/2005 | Adler et al. | |
| 2006/0291061 A1 | 12/2006 | Iyama et al. | |
| 2007/0106286 A1 | 5/2007 | Harschack et al. | |
| 2008/0287936 A1 | 11/2008 | Stinson et al. | |
| 2010/0135617 A1 | 6/2010 | Novak et al. | |
| 2011/0038580 A1 * | 2/2011 | Griffin | 385/33 |

* cited by examiner

REDIRECTING ELECTROMAGNETIC RADIATION

FIELD OF THE INVENTION

This invention is directed to devices, and their manufacture, for the lateral radiation of electromagnetic radiation (e.g., lasers).

BACKGROUND

Electromagnetic energy, such as laser light, is used to perform various medical procedures including the vaporization of hyperplastic prostate tissues. One optical device that is used in surgical tools that perform such medical procedures is a side fire optical fiber device, also known as a lateral delivery device.

Lateral delivery optical fiber devices are typically used to redirect delivered electromagnetic radiation in an off-axis direction from the longitudinal axis of the delivery fiber, typically at an angle of 70-90 degrees off axis. Conventional side fire optical devices operate by reflecting the electromagnetic radiation off of a beveled optical surface that is machined and polished directly upon the transmitting optical fiber conduit, exploiting total reflection at or below the critical angle as described by Snell's Law. The conditions for total reflection are typically maintained by protecting the output bevel with a circumferential protective cap typically made of fused quartz or fused silica. The redirected output laser light is transmitted through a transmitting surface on the protective cap to the surgical site.

During surgery, the surface of the cap is subjected to cycles of rapid heating and cooling as well as sustained heating. Thermal cycling can induce stresses in the cap that are large enough to induce fracturing, particularly where the cap harbors residual stress from manufacturing, i.e. the external cap has not been annealed following melt processing as is the case in U.S. Pat. No. 5,537,499 (Brekke), U.S. Pat. No. 5,562,657 (Griffin), U.S. Pat. No. 7,463,801 (Brekke and Brucker), and U.S. Pat. No. 8,073,297 (Griffin). Both transient and sustained high temperatures at the transmitting surface of the cap accelerate the endothermic absorption of alkali metal ions within the quartz that form the cap, lowering viscosity sufficiently to permit rearrangement of the amorphous glass into high crystobalite; the cap undergoes devitrification.

These thermally mediated failure modes are more problematic when newer surgical lasers that produce significantly higher average powers are utilized, e.g. 120 W holmium laser energy (2140 nm), 180 W "Greenlight" laser energy (523 nm), 200 W diode laser energy (980 nm), and further magnified when the device is involved in tissue contact surgery. The stresses in the side fire optical devices often result in the cap cracking, shattering or perforation by sloughing off of highly localized and intense devitrification.

Figures 1, 1A, 1B:
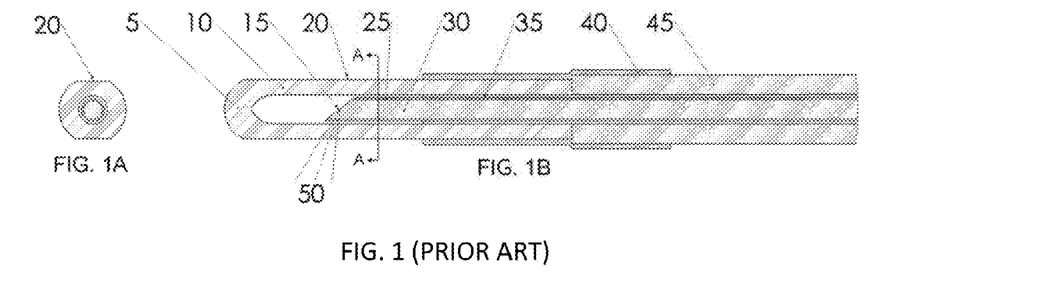
FIG. 1 is orthogonal, magnified side cross-sections (FIG. 1A and FIG. 1B) illustrating the essential features of prior art (adapted from Abe, et al.).

Lateral delivery optical fibers for surgery have been described and produced for decades. Early lateral delivery fibers were simple in construction FIG. 1: an optical fiber 30 polished at an off-axis angle 15 of between 35 and 40 degrees about which a closed end 5 transparent tube 10, akin to a tiny test tube is affixed (the tube is often called a "protective cap", the surface through which the light exits being referred to the "transmissive surface"). Deficiencies with this simple design were quickly recognized and strategies designed to mitigate these deficiencies were implemented with varying degrees of success. The example in FIG. 1 illustrates an embodiment of an invention first described in Japanese Pat. No. 61-64242 and later in U.S. Pat. No. 4,740,047 (Abe, et al.) where the original cylindrical transmissive surface of the cap, and the cap surface 180 degrees opposing the transmissive surface 20, are modified to planar surfaces.

Figure 2:
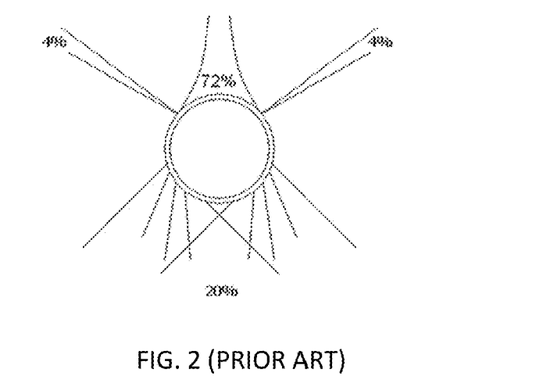
FIG. 2 is a magnified cartoon illustrating the variety of off-axis angles for misdirected rays, and the primary (desired) output for side fire fiber optic devices in prior art (adapted from Pon).
Figure 3A:
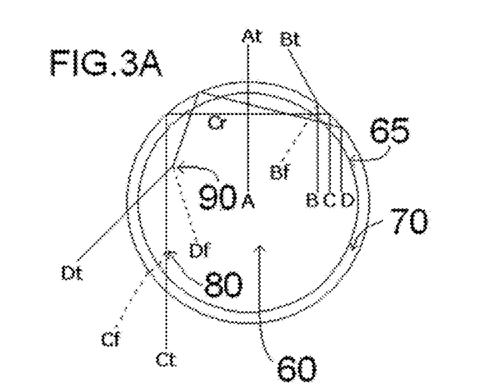
FIG. 3 are magnified cross-sectional cartoons depicting the various fates for rays of light within early prior art (FIG. 3A) and subsequent prior art (FIG. 3B) side fire fiber devices (adapted from Pon).
Figure 4:
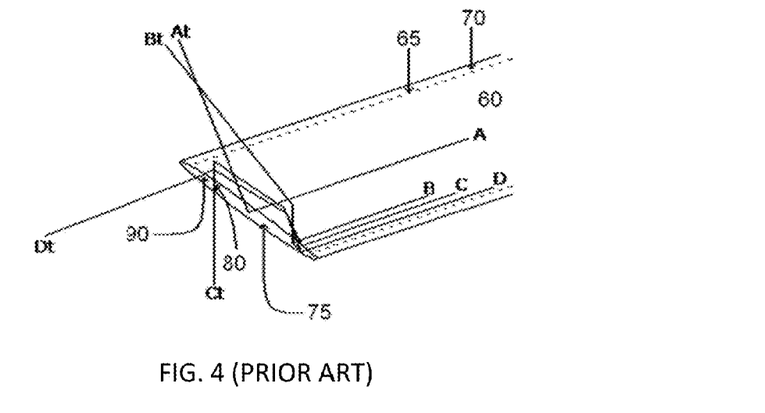
FIG. 4 is a magnified isometric cartoon of the reflecting tip of the lateral delivery optical device of FIG. 1 and FIG. 3A, providing another view of the fates for rays of light within prior art devices (adapted from Pon).

As illustrated in FIG. 2, some rays of light imparting the curved side of an optical fiber after reflecting from the bevel surface within the simplest lateral delivery fibers encounter angles at or near the critical angle for total reflection (rays C and D in FIG. 3A) as defined by Snell's Law such that a significant portion of the energy that encounters the reflective bevel tip does not exit the fiber in the desired direction, but undergoes complex reflections within the tip instead, eventually exiting in a variety of directions other than the desired direction, with roughly 20% of the errant energy leaking in roughly the opposite direction from the desired output. Referring to FIG. 3A and FIG. 4, reflected rays imparting the cylindrical cladding 70 to air interface near the outer edge of the fiber core 60, as represented by rays C and D, are completely reflected and encounter the cylindrical wall again at low angles, only to be reflected again until, at points 80 and 90, where the rays encounter the bevel face once more, they are refracted and transmitted Ct and Dt out of the fiber tip in the wrong direction. More central rays as represented by A and B, are refracted and transmitted by the cylindrical fiber's glass to air interface and transmitted At and Bt in the desired direction. All rays also undergo Fresnel reflections Af, Bf, Cf and Df upon ultimately exiting the fiber tip.

These complex reflections are repeated where the diameter of the fiber (glass diameter, usually the cladding) closely matches the diameter of the protective cap bore (which is not the case in Abe FIG. 1, due to the use of a relatively thick buffer coating of silicone 35 in optical fiber of the era), at the air to cap glass interface. Additional contributions to scattering in directions other than the intended output results from Fresnel reflection at the fiber core to cladding interface 65 (typically minor due to closely matched refractive indices), the cladding to air interface, the air to protective cap interface and the cap to working environment interface (again, minor due to the much closer match of the refractive indices of glass and saline irrigation fluid versus those for glass and air).

Additional distortion of the output results from the non-orthogonal off axis angle of emission and the cylindrical lens effects of the curved surfaces in the output pathway. In total, roughly 28% FIG. 2 of the energy imparting the fiber bevel exits at angles that are surgically useless, and potentially harmful, while the energy that is emitted in the desired direction is highly distorted. Rather than a round spot that diverges symmetrically, the spot is typically reminiscent of a crab with a roughly oval center (body) with radiating streaks (legs) and divergence is highly asymmetric.

Abe, et al. describe a strategy to mitigate the problem of unwanted reflections within the lateral fiber structure by eliminating the curvature of the cap outer diameter and equipping the transmissive surface with an antireflective coating and the surface 180 degrees opposing the transmissive surface with reflective coatings. This strategy does considerably reduce the output that is 180 degrees opposite of the desired direction but does not correct the distortion and fragmentation of the output in the desired direction. The expensive optical coatings are also short lived, being easily damaged in the surgical environment.

Figure 3B:
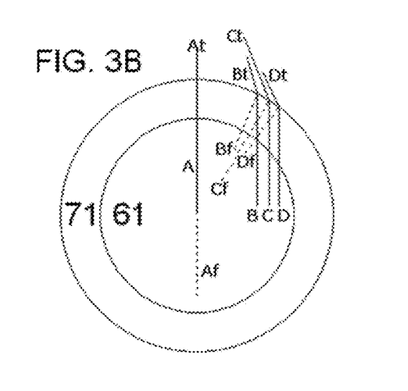

U.S. Pat. No. 5,428,699 (Pon) describes a more elegant, yet partial solution to the problem of unwanted reflections within the side fire fiber output FIG. 3B. Recognizing that the closely matching curvature of the fiber core and fiber cladding was the source of most of the exit angles at or near the critical angle, Pon pointed out that equipping the fiber with a thicker cladding 71 would greatly reduce these unwanted, complex reflections by displacing the glass to air interface away from the core 61. An embodiment of the invention described in Pon (Laserscope's LDD-Stat and other branding) was highly successful in the marketplace over the bulk of the '699 patent lifetime, in spite of the high cost resulting from using very expensive 1.4 CCDR (Cladding to Core Diameter Ratio) fiber, because the invention reduced the unwanted scatter output and distortions of the output spot by almost 75%.

Figure 5:
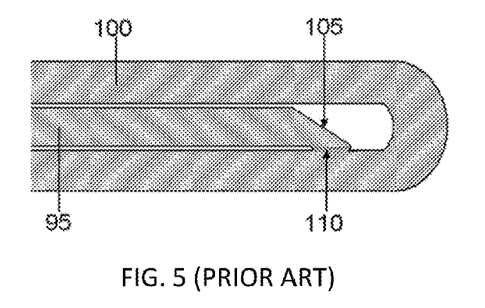
FIG. 5 is a magnified side cross-section view of prior art (adapted from Brekke).
Figure 6:
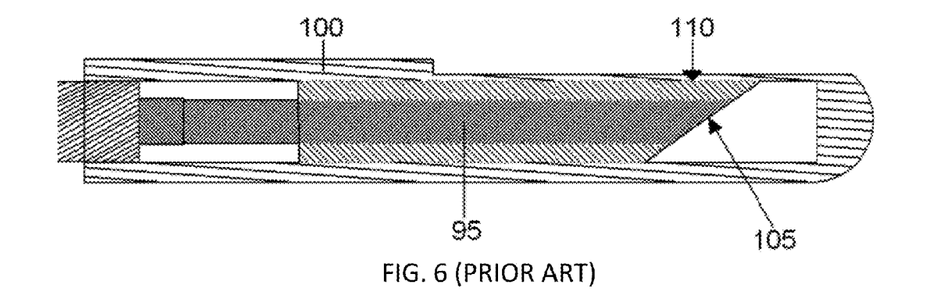
FIG. 6 is a magnified side cross-section view of prior art (adapted from Griffin).

Roughly contemporaneous with Pon, two patents, Brekke '499 FIG. 5 and Griffin '657 FIG. 6, taught another strategy for reducing unwanted reflections in side firing fibers: fusion of the fiber's outer glass diameter to the protective cap's inner diameter. Eliminating the large differences in refractive indices in the output path essentially eliminated the unwanted critical angle reflections (referred to as "Snell reflections" hereafter), Fresnel reflections and cylindrical distortions of the output. Essentially no back reflections exist for the inventions described and the output profiles are essentially oval with the relatively sharp edges typical of standard, axial fiber output profiles. Both inventions describe embodiments that may be produced with far lower cost fiber optic materials than required by Pon (1.1 CCDR and 1.05 CCDR) but both inventions also suffer the same flaw. Fusion 110 of the bevel tipped 105 fiber 95 to the cap 100, either directly (Brekke, FIG. 5) or through a glass sleeve (Griffin, FIG. 6), results in high residual stresses "frozen" within the assembly that cannot be removed; the fused features of the output are contiguous with heat labile polymers on the transmitting fiber optic conduit such that the assemblies cannot be thermally annealed.

These stresses were problematic at the higher average power settings of lasers in use a decade ago, where repeatedly and rapidly heating and cooling the side firing fiber caps amplified preexisting stresses and/or flaws, often causing fractures at the junctions of fused and un-fused portions of the assemblies. Modern surgical laser powers can deliver twice the average power of the former installed base, making the control of Snell and Fresnel reflections even more important and rendering inviable the solutions taught in '499, '657 and even '699.

Figure 7:
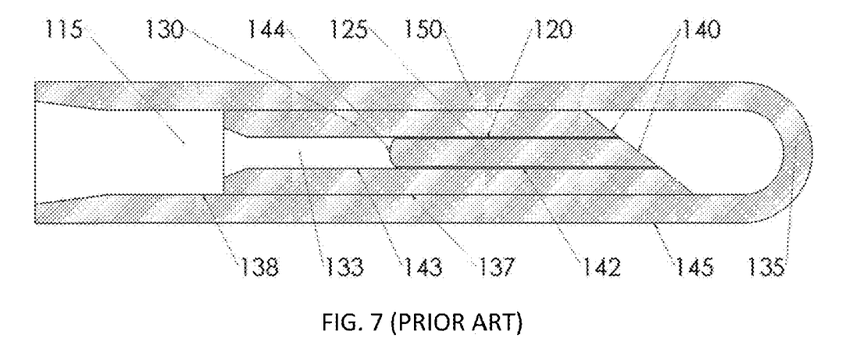
FIG. 7 is a magnified side cross-section view of prior art (adapted from Griffin).

Prior art '297 FIG. 7 teaches a side fire optical device for laterally redirecting electromagnetic radiation-comprising: a cap member 150 comprising a closed end section 135, a tube section having a bore 115, and a transmitting surface 145; a sleeve 130 received within the bore of the tube section, the sleeve including a bore 133 and an exterior surface 137 that is fused to a surface of the bore of the cap 138 member; and a fiber optic segment 125 comprising an exterior surface 142 that is fused to a surface of the bore of the sleeve 143, a beveled end surface 140 positioned adjacent the transmitting surface of the cap member and a receiving end 144 opposite the beveled end surface that is within the bore of the tube section, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap member and variations thereof. Minor Fresnel reflections remain due to the lower refractive index of the fiber optic segment cladding 120 relative to the fiber optic segment core 125 and the sleeve 130 and at the fuses surfaces (due to contamination, captured gases, differential surface chemistry, etc.).

In particular, the fiber optic segment 125 of the prior art illustrated in FIG. 7 must be produced from a very limited selection of standard optical fiber materials unless custom drawn optical fiber is utilized. Standard optical fiber raw materials for constructing the fiber optic segment 125 are produced with buffer coatings and jacket materials. These polymers that must be removed completely, without damaging the exterior surface 142 of the fiber optic segment least gas bubbles form in the fusion process. Custom draws of optical fiber typically require a large minimum order and command premium prices; in the current marketplace, a minimum order custom optical fiber for the prior art '297 would provide sufficient material for approximately 250,000 to 1 million assemblies, sufficient devices for supplying 100% of the US market for 1 to 4 years.

Side fire fibers that are currently available to surgeons are exclusively single use devices that are discarded post-operatively and cost as much as $900 each. More than one fiber is often required to achieve the surgical goal, particularly in benign prostatic hyperplasia (BPH) cases where the patient has been taking drugs such as Flomax for relief of BPH symptoms, the prostate gland is larger than 30 grams and/or the patient has had a prior prostate resection. The fiber optic conduit and laser connector represent roughly 95% of the materials costs and between 20% and 40% of the labor costs of producing a side fire fiber.

SUMMARY

Figure 8:
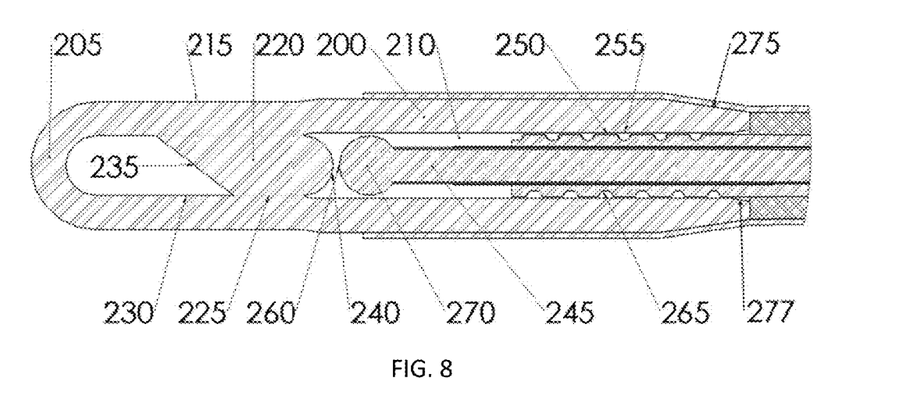
FIG. 8 is a magnified side cross-sectional view of a lateral delivery optical device in accordance with embodiments of the invention.

A first embodiment includes a side fire optical device for directing electromagnetic radiation. The side fire optical device, for example as shown in FIG. 8, includes a tube portion 200 having a one-piece construction, including a guide section and an open-end section, the open-end section and the guide section divided by a lens 240, the open-end section including a bore 210 which terminates at the lens 240, the open-end section shaped to receive a fiber optic cable 245, the guide section including a light path from the lens to a reflecting surface 235 and then to a transmitting surface 215, the reflecting surface 235 configured to direct electromagnetic radiation from the lens 240 through the transmitting surface 215 at a side of the tube portion.

A second embodiment includes a process for manufacturing a side fire optical device comprising. The process includes providing a tube made of an optically transparent material, the tube having an inside diameter; providing a solid cylinder having an outside diameter less than 1 mm smaller than the inside diameter of the tube, the solid cylinder having a first end that terminates in a beveled surface, the solid cylinder having a second end opposing the first end that terminates in a lens; positioning the solid cylinder within the tube; then thermally fusing the solid cylinder and the tube to form a tube portion of the side fire optical device; and then annealing the tube portion at a temperature above about 900° C.

A third embodiment includes the surgical use of a side fire optical device. The surgical use includes the application of a side fire optical device, for example as shown in FIG. 8, which includes a tube portion 200 having a one-piece construction, including a guide section and an open-end section, the open-end section and the guide section divided by a lens 240, the open-end section including a bore 210 which terminates at the lens 240, the open-end section shaped to receive a fiber optic cable 245, the guide section including a light path from the lens to a reflecting surface 235 and then to a transmitting surface 215, the reflecting surface 235 configured to direct electromagnetic radiation from the lens 240 through the transmitting surface 215 at a side of the tube portion; where the side fire optical device does not heat above about 70° C., 60° C., 50° C., or 40° C. during the surgical use. Preferably, wherein the side fire optical device does not heat while conducting electromagnetic radiation to a surgical site. More preferably, wherein the side fire optical device does not cause contact-based thermal denaturation of proteins.

Another embodiment can include a control device that affects a distance between the lens and the fiber optic cable, thereby affecting the focus of a transmitted electromagnetic spot. Whereby, the actuation of the control device narrows or widens the transmitted electromagnetic spot allowing for a user to transition between, for example, ablative surgical use of the electromagnetic radiation and cauterization.

Yet another embodiment includes a fiber optic bundle containing a plurality of fiber optic strands coupled to the side fire optical device.

Still another embodiment includes a side fire optical device that includes both emission and detection optical fibers.

BRIEF DESCRIPTION OF THE FIGURES

For a more complete understanding of the disclosure, reference should be made to the following detailed description and accompanying drawing figures wherein:

FIG. 10 are magnified side cross-sectional views of a lateral delivery optical device in accordance with embodiments of the invention.

FIG. 11 is a magnified side cross-sectional view of a lateral delivery optical device in accordance with embodiments of the invention.

FIG. 17 presents three orthogonal cross-sections of a multi-fiber variant of a preferred embodiment.

While specific embodiments are illustrated in the figures, with the understanding that the disclosure is intended to be illustrative, these embodiments are not intended to limit the invention described and illustrated herein.

DETAILED DESCRIPTION

The herein provided embodiments include a side fire optical device ("cap") for redirecting electromagnetic radiation, methods of their manufacture, and methods of their use. These embodiments minimize potential Fresnel reflections at fused surfaces and eliminate Snell and Fresnel reflections in a self-contained lateral output assembly (within which a transmitting optical fiber conduit may be subsequently attached), the construction of which involved lower cost raw materials and fewer manufacturing steps; provide a side fire fiber where the protective cap can be replaced interoperatively and even intraoperatively; and provide mechanisms and processes for altering the size or shape of the output spot without altering the lateral fiber design. Typically, an invariable output profile requires surgeons to hold a fiber's output surface (transmissive surface) quite near, but not in contact with, target tissue for the best vaporization results and, alternatively, to hold the fiber a few millimeters away from the target tissue if coagulation is requires, e.g. for cauterization of a "bleeder". Notably, these instructions are extremely difficult to comply in the real world of surgery where visualization is by way of a fiber optic imaging bundle within a cystoscope and fiber positioning is at best indirectly controlled by way of cystoscope position and a pin-vice-like device located on the fiber at about 40 cm proximal to the fiber output. Therefore, the herein provided embodiments further provide mechanism and process for output spot profile alteration, either pre-operatively or intraoperatively.

The invention claimed and described herein includes a strategy for forming optical fiber caps for lateral redirection of laser light or light for spectroscopy and various assemblies thereof. In a preferred embodiment, a optically polished surface for redirecting electromagnetic energy in accordance with Snell's Law (a bevel surface) is produced upon a short cylinder of uncoated (unclad) and optically transparent material (where in prior art this surface is produced upon an optical fiber or segment of optical fiber) that is fused within a tiny test-tube of the same material, near the closed end, producing an enclosed space of air or partial vacuum between the bevel surface and the closed end of the tube while retaining most of the open bore of the test tube: a lateral cap device for redirecting electromagnetic radiation (e.g., FIG. 8).

A transmitting fiber optic conduit, equipped on one end for coupling to a light source, typically a laser, and the other end equipped with a flat polished output ("laser fiber"), may be inserted within the open bore of the lateral cap to produce a side fire fiber with utility in laser surgery, ordinance ignition and spectroscopy.

Alternatively, the short cylinder of uncoated optical material may be equipped with a lens for coupling the output of laser fiber and the laser fiber may be similarly equipped with a lens-end or other optical treatments such as tapers for coupling to the lateral cap. Lenses within the lateral cap structure may be cylindrical, hemispherical, spherical sections, aspheric or meniscus lenses.

Embodiments of the invention include addition of a hollow metallic shroud surrounding the lateral cap, equipped with an output window for the redirected light from the lateral cap, and secured to the optical fiber buffer coating (sometimes called "jacket") for protection of the lateral cap element. Unlike prior art side fire fibers with the delicate bevel tipped optical fibers, providing a means for replacing caps that wear out in use is greatly simplified where the laser fiber tip is relatively rugged: flat polished or lens-ended. Modifications of the metallic shroud to permit reversible coupling between a section that is secured about the lateral cap and a section secured to the laser fiber buffer enable the lateral cap to be easily replaced.

Further embodiments of the invention are enabled by extending the metallic shroud segment, unattached to the fiber buffer, to a control device located some distance along the laser fiber where it is affixed to one half of the control device, where the other half of the control device is affixed to the fiber buffer, enabling adjustment of the distance between the laser fiber output and the lateral cap input for external control of the delivered lateral spot size.

Among the objects of the present invention are the following:

To provide a new and useful method of producing self-contained lateral cap devices for redirecting electromagnetic radiation when attached to laser fibers, at angles roughly orthogonal to the original axial output;

To provide a new and useful construct for redirecting electromagnetic radiation when attached to laser fibers, at angles roughly orthogonal to the original axial output where reflections and distortions of the output are essentially eliminated;

To provide a new and useful construct for redirecting electromagnetic radiation when attached to laser fibers where a variety of beam shaping elements may be exploited, within the lateral cap design and for the laser fiber coupling to the lateral cap;

To provide a new and useful construct for redirecting electromagnetic radiation when attached to laser fibers where the lateral cap may be replaced during a surgical session and/or between surgical sessions; and To provide a new and useful construct for redirecting electromagnetic radiation when attached to laser fibers where the lateral output characteristics may be altered during surgery without the need to remove the fiber from the endoscopic device.

The novel features that are considered characteristic of the invention are set forth with particularity in the appended claims. The invention itself, however, both as to its structure and its operation together with the additional objects and advantages thereof will best be understood from the following description of the preferred embodiments of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the description of the invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

Embodiments of the present invention FIG. 8 are directed to a laser energy delivery device for laterally redirecting electromagnetic radiation comprising: a cap member 200 comprising a closed end section 205, a tube section having a bore 210, and a transmitting surface 215; and a solid cylindrical segment 220 comprising an exterior surface 225 that is fused to a surface of the bore of the cap 230, a beveled end surface 235 positioned adjacent the transmitting surface of the cap member and a receiving end 240 opposite the beveled end surface, wherein the beveled end surface is angled relative to a longitudinal axis of the fiber optic segment such that electromagnetic radiation propagating along the longitudinal axis of the fiber optic segment is reflected by the beveled end surface at an angle that is transverse to the longitudinal axis and through the transmitting surface of the cap. The receiving end of the solid cylinder that partially fills the cap bore may be a flat mating surface for coupling a fiber optic segment or it may be curved or sculpted to act as a lens 240 for shaping and receiving the transmission of the fiber optic conduit 245 delivering energy to the cap device. The fiber optic conduit comprises an exterior surface 250 that may be equipped with grooves or pits 265 for adhesion to the surface of the open bore of the cap 255 and positioned in contact with or nearly in contact with the flat or curved end of the solid cylinder 240 and the fiber optic conduit's transmitting surface may be flat, curved or shaped 260 to modify the output profile. The beveled end surface is angled relative to a longitudinal axis of the solid cylinder (and thus, the fiber optic conduit) such that electromagnetic radiation propagating along the longitudinal axis of the solid cylinder is reflected by the beveled end surface at an angle that is transverse to the longitudinal axis and through the transmitting surface of the cap member 215.

Unlike the invention described in prior art '297, the current invention utilizes low cost and readily available fused quartz (or fused silica) rod stock for producing the solid cylindrical element and does not utilize an intermediate sleeve element. Herein it was found that the elimination of the sleeve element 130 that is utilized in prior art affords greater space 210 within the cap bore, enabling the use of a transmitting optical fiber conduit equipped with a ball lens 270 or an up-tapered fiber for altering the characteristics of the light delivered to the solid cylindrical element 220. Flexibility in employing myriad transmitting optical fiber conduit designs permits greater control of the output spot profile relative to prior art, without altering the optical design of the invention: the lateral cap device.

More importantly, replacing the fiber segment of prior art '297 (having a core with a refractive index of 1.457 (fused silica) that is surrounded by a fluorine-doped cladding with a lower refractive index of 1.44 (NA=0.22) with the solid cylindrical element was found to significantly reduces the reflected component of the light exiting the fiber by way of reflection from the beveled planar face. Notably, the Fresnel reflections in '297 become large within the outer 3% of the fiber core, e.g.

almost 3% for rays at exiting at 97% of the fiber core radius, almost 10% at 98% of the radius or almost 25% at 98.5% of the radius, and become total internal reflections for the outer ~1.2% of the core.

The total reflected energy due to the light transitioning the cladding in the '297 patent is approximately 2% greater than that of the herein presented invention. While 2% is a relatively small improvement, any energy not directed to doing surgical work causes structural damage to the device, for example by raising the fiber tip (cap) temperature and facilitating tissue adhesion. Further, in that the reflections that are eliminated emanate from a well-defined geometric portion of the prior art, that energy is far less diffuse than the bulk of other reflections that are eliminated in '297, and is therefore far more problematic. A truly efficient fiber, such as disclosed herein, can remain cool and avoid thermal damage to both the fiber and surrounding tissues during use (e.g., during surgical use).

Figures 10, 10B:
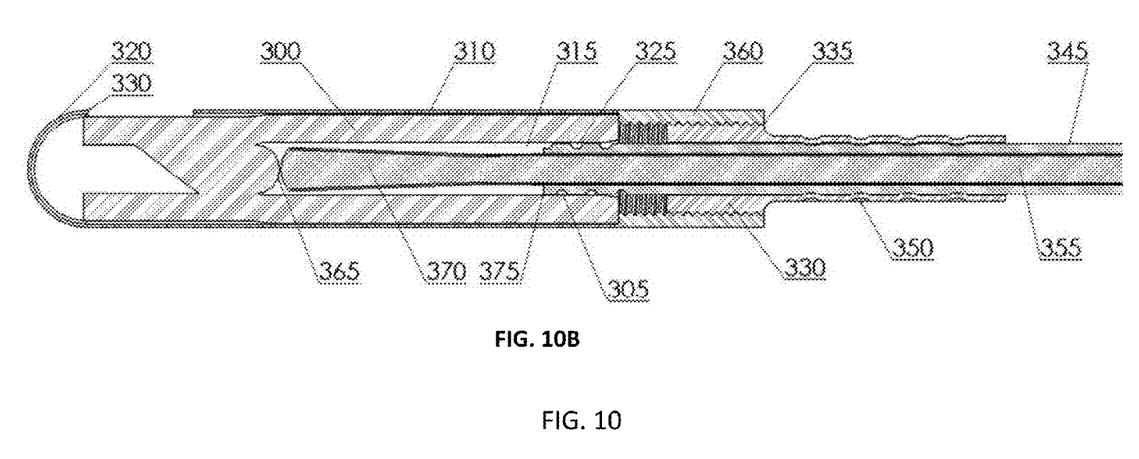
Figure 10A:
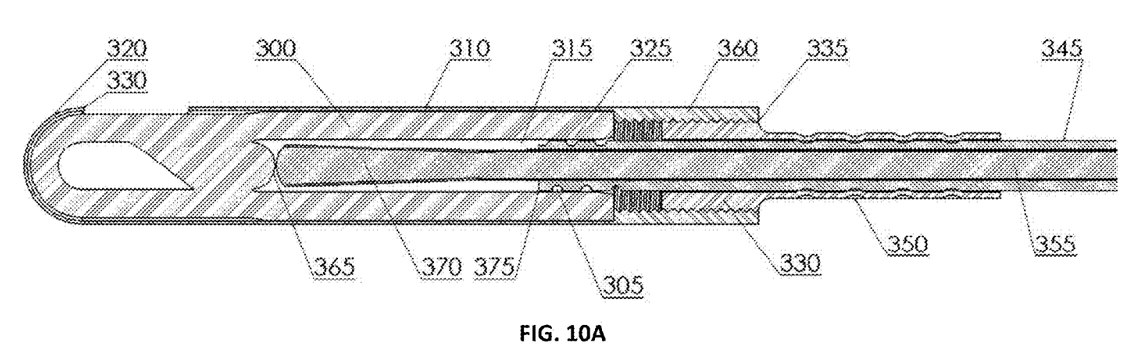
FIG. 10A includes a closed end with, preferably a vacuum bubble adjacent to the reflecting surface, FIG. 10B omits the closed end of the tube while maintaining the end within the protective metal tube.

Another example of the invention, FIG. 10, includes the assembled lateral delivery cap member 300 is housed within a protective metal tube 310 that is closed on one end 320, or partially closed, and equipped with an opening within the cylindrical wall 330 that is positioned adjacent to the transmitting surface. A male threaded portion of a metal crimp section 330 can be secured by crimping 350 (or other means) to the outer polymer coating (buffer) 345 of the optical fiber conduit 355 in addition to securing the roughened or grooved portion of the optical fiber buffer 305 within the open bore 315 of the transmissive protective cap with adhesive around 325. The male threaded crimp section mates within the female threaded section 360 at the open-end of the protective metal tube covering the lateral delivery cap. FIG. 10 also illustrates the use of an up-tapered fiber 370 for delivering optical energy of reduced divergence to the receiving face 365 of the lateral fiber cap.

Figures 11, 11B:
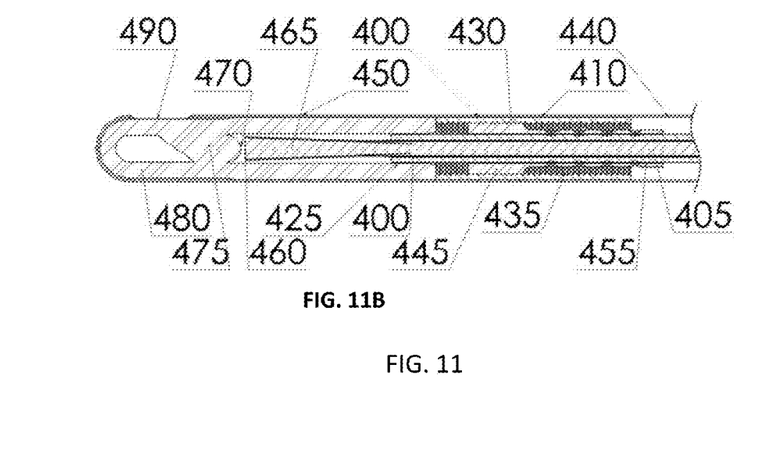
Figure 11A:
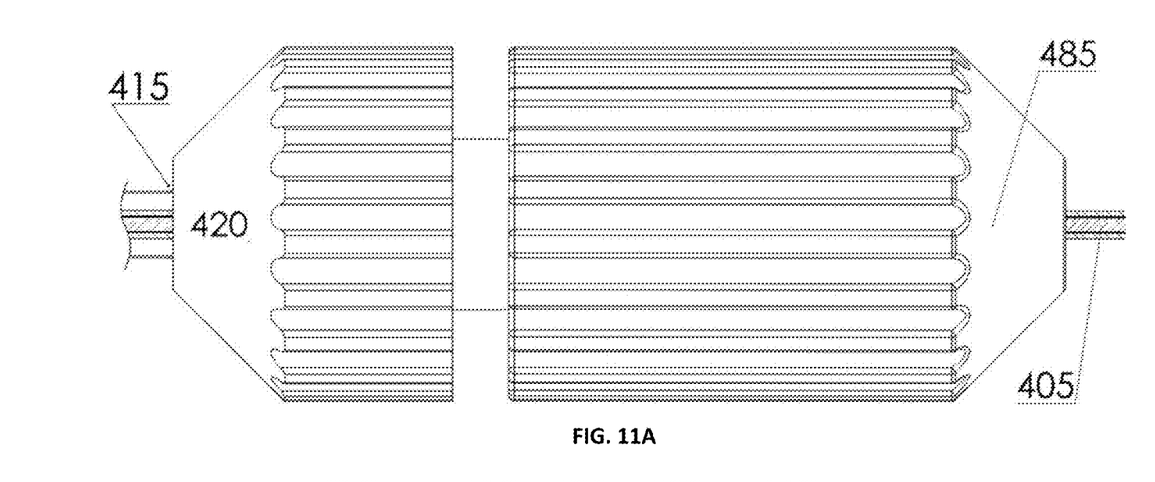
FIG. 11A includes a control device and FIG. 11B includes a lateral delivery optical device used with the control device.

Still another example, FIG. 11, includes an extension cannula 440 coupled to the metal protective cap 450 by way of a threaded coupler 430 within the bore 400 of the metal protective cap and the bore 410 of the extension cannula, with the extension cannula extending a length of the transmitting optical fiber conduit 405 sufficient to traverse the length of the working channel within a cystoscope. The proximal end of the extension cannula 415, outside of the cystoscope port, is affixed to one half 420 of a control device. Unlike the examples depicted in FIGS. 8 and 10, the buffer 400 of the delivery end of the transmitting fiber optic conduit is not equipped with grooves and is not adhered to the inside wall 425 of the glass cap bore such that the female threads 435 of the threaded coupler 430, in concert with the male threaded portion 445 of the metal crimp section 455, provide a means of adjusting the gap between the transmitting face 460 of the up-tapered fiber optic conduit 465 and the receiving face 470 of the solid cylindrical element 475 fused within the glass protective cap 480 via rotation of the transmitting optical fiber conduit 405 affixed within the second half 485 of the control device situated outside of the cystoscope working channel port. Through rotating one half of the control device, relative to the other half, the gap separating the transmitting face of the fiber optic conduit 460 and the receiving face of the fused lateral cap assembly 470 may be narrowed or widened, altering the lateral output spot size at the glass cap transmitting surface 490. Alternatively, the threads of the threaded coupler and the threads of the metal crimp section may be removed and the adjustment mechanism, such as threads, provided within the control device.

Figure 9:
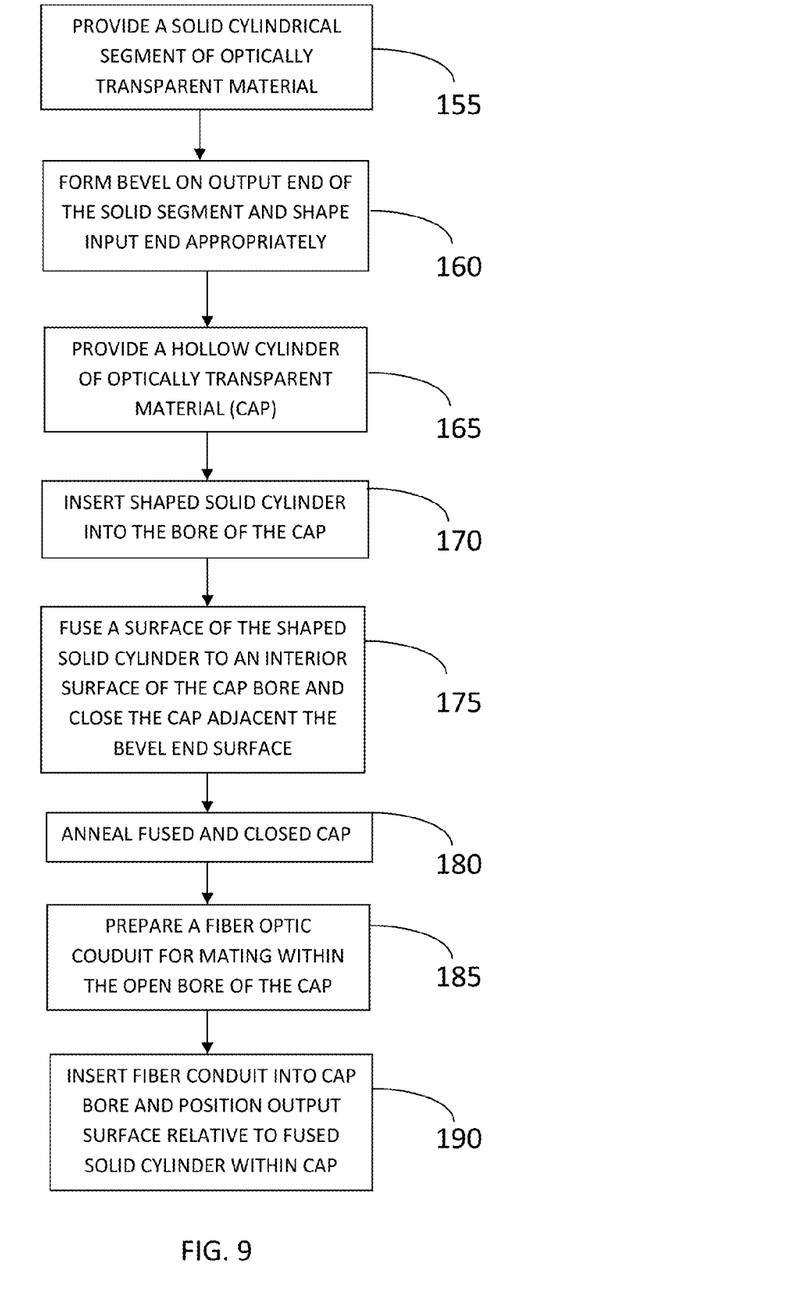
FIG. 9 is a flowchart depicting the essential steps required to produce embodiments of the invention.
Figure 12:
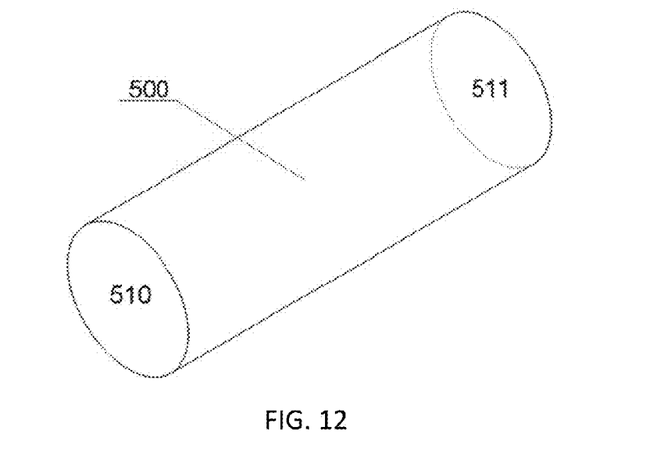
FIG. 12 is a magnified isometric view of a raw material component for producing all embodiments of the invention.
Figure 13:
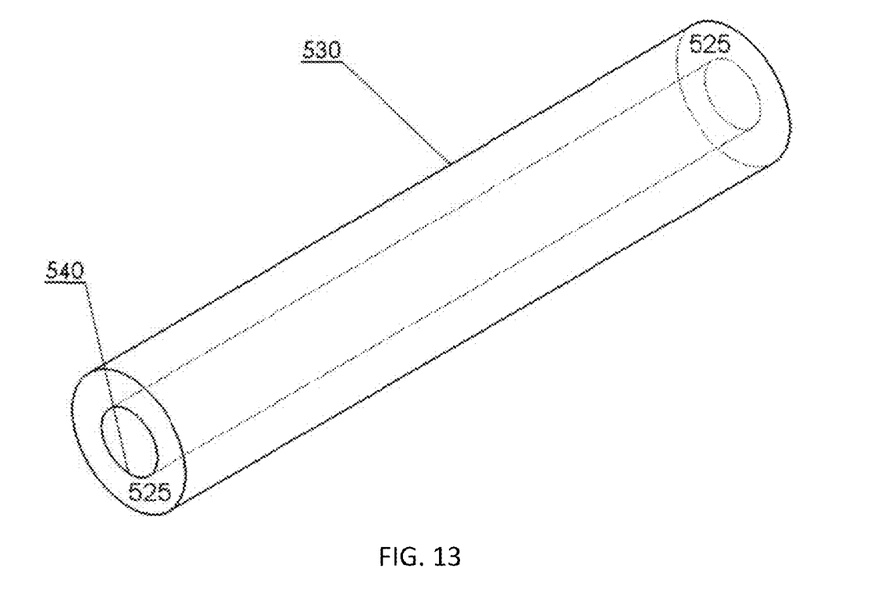
FIG. 13 is a magnified isometric view of a raw material component for producing all embodiments of the invention.
Figure 14A:
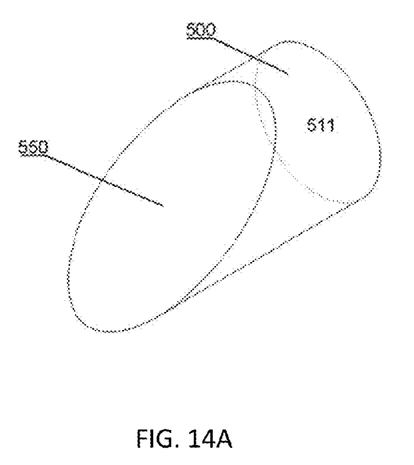
FIG. 14 provides a magnified isometric views (FIG. 14A side and FIG. 14B top) of a raw material component (FIG. 12) processed for producing embodiments of the invention and a magnified top view of an alternatively processed component (FIG. 12) for producing embodiments of the invention.
Figure 14B:
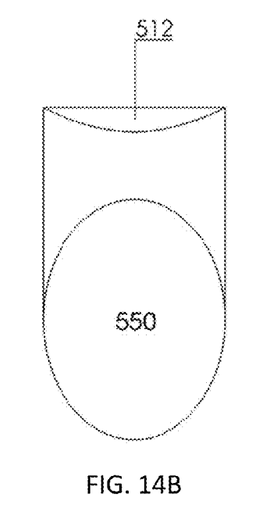

Another embodiment of the herein presented invention is a method of manufacturing the lateral cap device. In one example, FIG. 9 depicts five manufacturing steps 155-175 to produce the lateral cap device and subsequent steps 180-190 for producing a basic surgical device. FIG. 9 is a flowchart illustrating steps for manufacturing embodiments of a lateral delivery cap optical device described above. Initially, at steps 155 and 165, a solid cylindrical, transparent segment (FIG. 12), having a cylindrical surface 500 and two planar surfaces 510 and 511 and a hollow cylindrical, transparent segment—the cap element—(FIG. 13), having an outer cylindrical surface 530, an inner cylindrical surface 540 and two planar surfaces 525 are provided, preferably made of fused quartz (and preferably electrically fused quartz) or fused synthetic silica. The solid cylindrical segment (FIG. 12) and the cap precursor (FIG. 13) can be formed in accordance with any of the embodiments described above. Initially, the solid cylindrical segment is a straight section of rod, as shown in FIG. 12. In one embodiment FIG. 14A, the receiving end 511 of the solid cylindrical element remains a flat, optically polished surface. In another embodiment FIG. 14B, the receiving end 512 of the solid cylindrical element is either formed into a lens or a lens is attached to the receiving end 512, illustrated as a cylindrical lens in FIG. 14B. The lens formed or attached to the solid cylindrical element may be a cylindrical lens in any orientation, a hemispherical lens or partial spherical lens, a meniscus lens or aspheric lens.

At step 160 a beveled optical surface 550 (FIGS. 14A and 14B) can be formed at the reflection end 510 (FIG. 12) of the solid cylindrical element such that the angle of the bevel lies at the critical angle for the worst case ray of light delivered to the bevel surface, through the receiving surface 511, regardless of treatments to the receiving surface, e.g. 240 in FIG. 8, or the delivery surface 260 in FIG. 8 or numerical aperture reduction by way of tapering 370 in FIG. 10 within of the transmitting optical fiber conduit 355, such that all light rays imparting the bevel surface 550 (FIGS. 14A and 14B) will be totally reflected in a lateral direction relative to the axis of the transmitting optical fiber conduit. In one embodiment of the cap member, a chamfer 277 (FIG. 8) is formed at the optical fiber conduit receiving end to form a chamfered opening to the open bore 255 and/or a chamfer 275 is formed on the outer diameter of the cap member.

Figure 15:
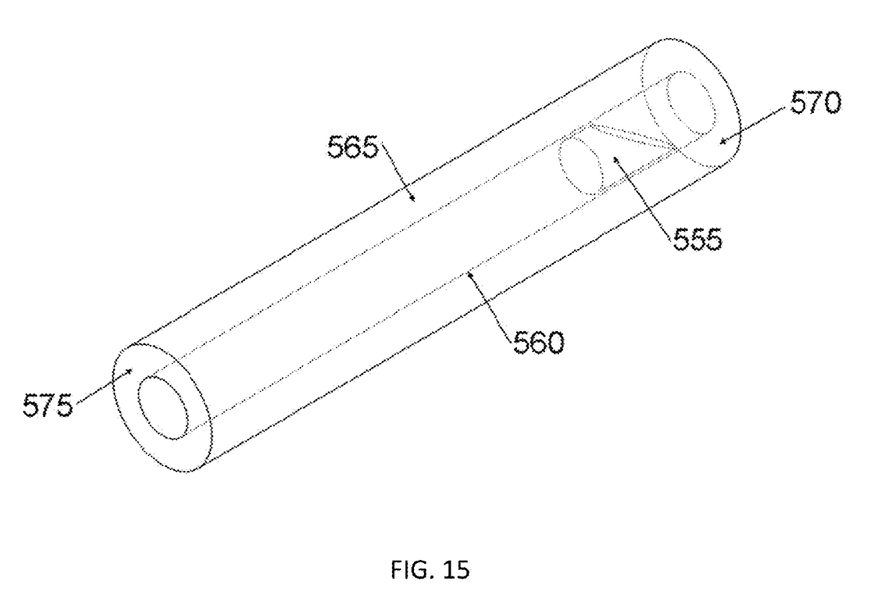
FIG. 15 is a magnified isometric view of one step for producing embodiments of the invention.

At step 170, the shaped solid cylindrical element 555 is inserted into the bore 560 of the cap element 565, near the planar face 570, as shown in FIG. 15. At step 175 (FIG. 16), an exterior and cylindrical surface 600 of the shaped solid cylindrical element 605 is fused to an interior surface 610 of the bore 615. The fusion of the shaped solid cylindrical element 605 to the cap 625 may be accomplished using conventional techniques. In one such technique, the shaped solid cylindrical element 605 and the cap 625 are rotated under laser illumination. The laser is scanned down the cap 625 from position 630 to 640, slightly shrinking the bore 615 until fusion is accomplished and the cap is closed 650. Alternative techniques to fuse the shaped solid cylindrical element 605 to the cap 625 include furnace fusion, flame fusion, low temperature glass melt and other conventional techniques. Laser and/or flame fusion techniques are preferred, enabling, for example, fusion and closing of the cap in a single production step.

For applications where the operating medium is of low refractive index, e.g. in air, or where the optical output of the lateral optical device may serve as input to a second, similar device, e.g. absorption spectroscopy probe, it may be desirable to produce a flat transmissive surface upon the cap cylindrical outer diameter, similar to that depicted in FIG. 6.

Figure 16:
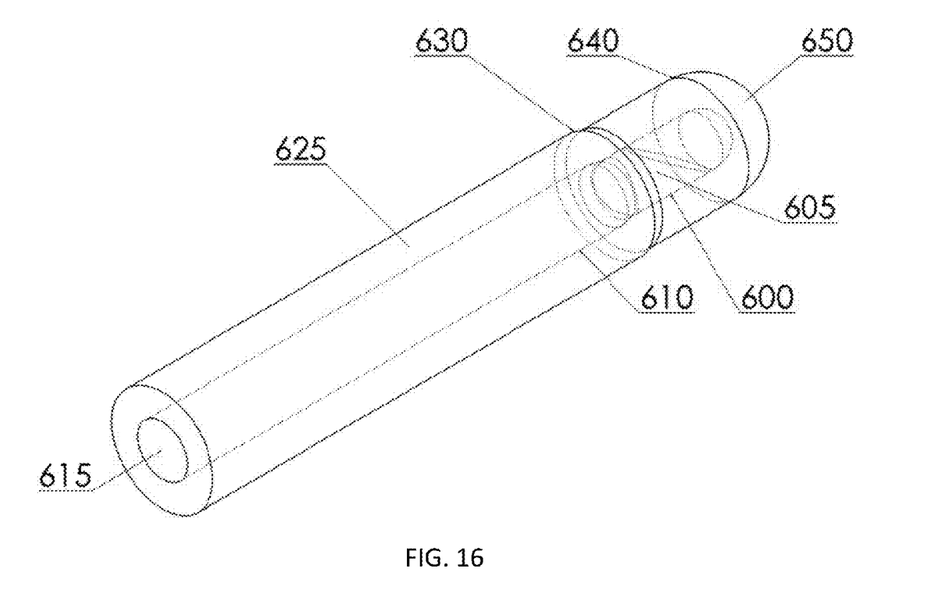
FIG. 16 is a magnified isometric view depicting the essential elements of the invention.

In accordance with embodiments of the method, at step 180 the assembled lateral optical device FIG. 16 is annealed at a temperature in excess of 1100° C. This process relieves the stresses formed in the components of the lateral optical device FIG. 16 due to the polishing, beveling, fusion and cap closing processes as well as optional processes such as lens formation, lens attachment and chamfering for example. Once annealed, the lateral optical device becomes more capable of withstanding the redirecting of high powered electromagnetic radiation and far more capable of withstanding the rapid thermal cycling inherent in surgical use as compared to prior art electromagnetic radiation redirecting devices.

Figure 17A:
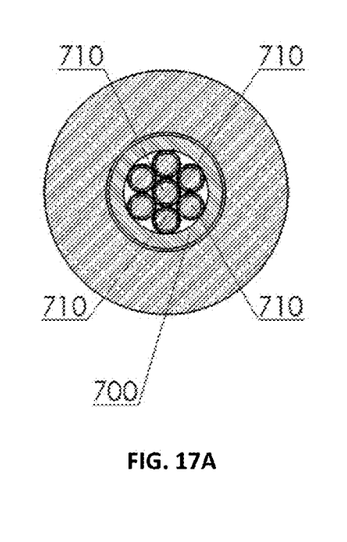
FIG. 17A is a horizontal cross-section.
Figures 17B, 17C:
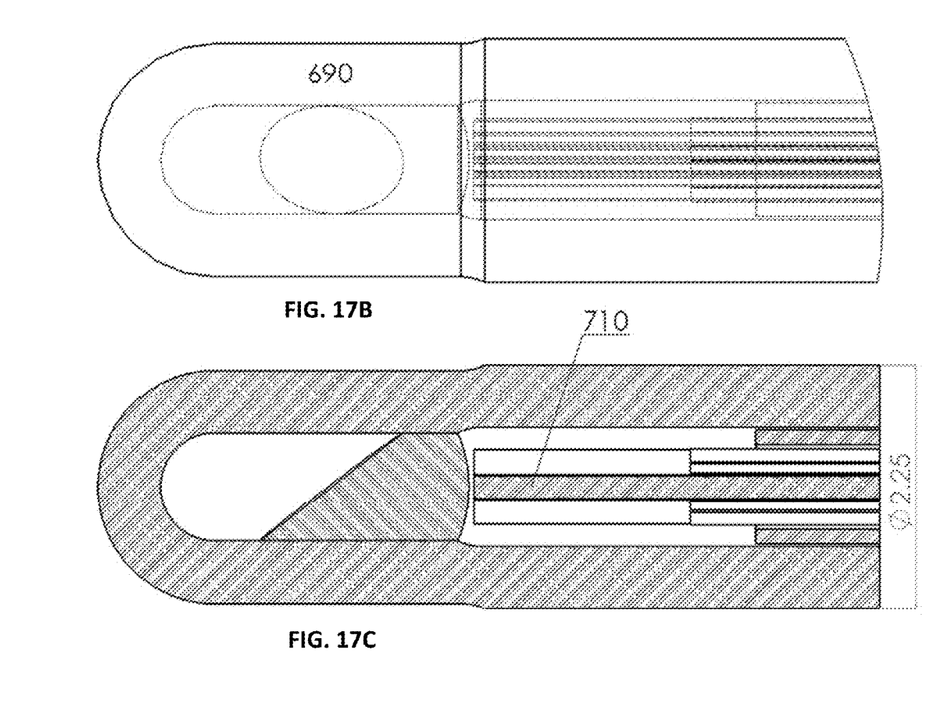
FIG. 17B and FIG. 17C are longitudinal cross-sections.

In another embodiment as depicted in FIG. 17, a device 690 for redirecting electromagnetic energy may employ a fiber optic bundle 700 containing discrete fiber optic strands 710 that may be coupled to one of more laser energy sources, imaging systems and/or analytical instrumentation, thereby permitting multiple functions within a single device. In one example, a single fiber optic 710 may carry a surgical wavelength of laser light that is suitable to, for example, vaporize and/or fragment kidney stones while another fiber optic 710 transmits laser light having a surgical wavelength that is suitable for coagulation. In another example, one of the fiber optics 710 can carry laser light having a wavelength that is suitable for diffuse reflectance while one or more of the other fiber optics 710 are used to collect the reflectance for spectral analysis. As a result, the device 690 can be used to both analyze the tissues of the patient and treat those tissues without having to change devices. Thus, the device 690 can be configured to have one or more fiber optics 710 that can be used to provide optical screening for one or more cancers or other diseases and other fiber optics 710 that are configured to perform surgery.

In still another example, the device 690 may be used to locate and treat vulnerable plaque (a semi-fluid inclusion in the arterial wall that causes fatal heart attacks when it escapes) in coronary arteries. Here, one or more of the optical fibers 710 are connected to a rapidly tunable visible laser (e.g., 200 nm scan range). The laser light is delivered from an emission fiber to the arterial wall through the device 690, which redirects the light to an arterial wall, which it penetrates. When it encounters vulnerable plaque the scattered laser light is altered in a manner that is detectable when delivered to a spectrometer by the surrounding fiber optics 710 (e.g., detection optical fiber) of the device 690. If more than one ring of fibers 710 is used to collect the scattered light, different depths can be scanned, giving a low resolution "image" of the plaque profile. While this alone is of great value, one may also use other fiber optics 710 of the bundle 700 to deliver a surgical wavelength of laser light that can "cook" the vulnerable plaque and make it a solid material that cannot escape through the artery wall.

In still yet another example, one of the fiber optics 710 of the device 690 can be used to deliver Raman excitation (e.g., via an emission optical fiber) while a different optical fiber 710 of the bundle 700 collects the florescence from prostate tissue. If the returned spectrum (e.g., via a detection optical fiber) indicates cancerous tissue, other fiber optics 710 of the fiber optic bundle 700 that are not being used for spectroscopy can deliver surgical wavelengths of laser light to kill the cancerous tissue. As a result, the device 690 can be used to provide real-time targeting of deceased tissue while sparing healthy tissue.

In yet another example, each of the fiber optic element 710 in the bundle 700 can be connected to a high energy pulse Nd:YAG laser and each of the seven Nd:YAG lasers feeds a similar bundle of seven fibers connecting to seven devices 690. Accordingly, each device 690 is fed by seven Nd:YAG lasers and each Nd:YAG laser supplies a portion of its energy pulse to each of the seven devices 690. Such an arrangement would have utility as a highly redundant laser ordinance ignition system for seven separate charges. For any single charge to fail to ignite, all seven Nd:YAG lasers must fail.

Although the present invention has been described with reference to preferred embodiments, workers skilled in the art will recognize that changes may be made in form and detail without departing from the spirit and scope of the invention.

What is claimed is:

1. A side fire optical device for directing electromagnetic radiation, comprising:
    a tube portion having a one-piece construction consisting of fused quarts and/or fused silica, including
        a guide section and an open-end section,
        the open-end section and the guide section divided by a lens,
            the open-end section including a bore which terminates at the lens, the open-end section shaped to receive a fiber optic cable,
            the guide section including a light path from the lens to a reflecting surface and then to a transmitting surface, the reflecting surface configured to direct electromagnetic radiation from the lens through the transmitting surface at a side of the tube portion.

2. The side fire optical device of claim 1, wherein the tube portion is a one-piece construction of annealed glass.

3. The side fire optical device of claim 1, wherein the lens is convex.

4. The side fire optical device of claim 1, wherein the lens includes a focal point along the light path and selected from the locations consisting of (a) between lens and the reflecting surface, (b) between the reflecting surface and the transmitting surface, and (c) at about the reflecting surface.

5. The side fire optical device of claim 1, wherein the lens includes a focal point beyond the transmitting surface.

6. The side fire optical device of claim 1, wherein the reflecting surface is angled relative to a longitudinal axis of the bore such that electromagnetic radiation propagating along the longitudinal axis of the bore is reflected by the reflecting surface at an angle that is transverse to the longitudinal axis and through the transmitting surface.

7. The side fire optical device of claim 6, wherein the reflecting surface is angled at about 35 to about 45 degrees relative to the longitudinal axis.

8. The side fire optical device of claim 1, wherein the tube portion includes a transmission of electromagnetic radiation which occurs without heating the tube portion.

9. The side fire optical device of claim 1 further comprising a coupling that permits the reversible connection of a fiber optic cable.

10. The side fire optical device of claim 1 further comprising a housing that incompletely encompasses of the tube section, wherein the housing does not encompass the transmitting surface.

11. The side fire optical device of claim 10, wherein the housing completely encompasses the open-end section while permitting the reversible connection of a fiber optic cable.

12. The side fire optical device of claim 1 further comprising a fiber optic cable terminating within the bore of the open-end section.

13. The side fire optical device of claim 12, wherein the fiber optic cable terminates in a ball lens, a tapered fiber, or a lens-equipped taper fiber.

14. A side fire optical device for directing electromagnetic radiation, comprising:
    a tube portion having a one-piece construction, including
        a guide section and an open-end section, the open-end section and the guide section divided by a lens, the open-end section including a bore which terminates at the lens, the open-end section shaped to receive a fiber optic cable, the guide section including a light path from the lens to a reflecting surface and then to a transmitting surface, and a vacuum bubble adjacent to the reflecting surface, and outside of the light path; the reflecting surface configured to direct electromagnetic radiation from the lens through the transmitting surface at a side of the tube portion.

15. A process for manufacturing a side fire optical device comprising:

providing a tube consisting of fused quartz or fused silica, the tube having an inside diameter;

providing a solid cylinder having an outside diameter less than 1 mm smaller than the inside diameter of the tube, the solid cylinder having a first end that terminates in a beveled surface, the solid cylinder having a second end opposing the first end that terminates in a lens; the solid cylinder consisting of fused quartz or fused silica;

positioning the solid cylinder within the tube; then thermally fusing the solid cylinder and the tube to form a tube portion of the side fire optical device; and then annealing the tube portion at a temperature above about 900° C.;

wherein the tube portion consists of fused quartz and/or fused silica.

16. The process for manufacturing a side fire optical device of claim 15, wherein the tube is made of a silica glass; and wherein the solid cylinder is made of a silica glass.

17. The process for manufacturing a side fire optical device of claim 15, wherein the tube portion is annealed at a temperature above about 1100° C.

18. A process for manufacturing a side fire optical device comprising:

providing a tube made of an optically transparent material, the tube having an inside diameter;

providing a solid cylinder having an outside diameter less than 1 mm smaller than the inside diameter of the tube, the solid cylinder having a first end that terminates in a beveled surface, the solid cylinder having a second end opposing the first end that terminates in a lens;

positioning the solid cylinder within the tube; then thermally fusing the solid cylinder and the tube to form a tube portion of the side fire optical device; forming a vacuum bubble adjacent to the beveled surface and then annealing the tube portion at a temperature above about 900° C.

* * * * *